United States Patent [19]
Shibanuma

[11] Patent Number: 5,642,157
[45] Date of Patent: Jun. 24, 1997

[54] ELECTRONIC ENDOSCOPE APPARATUS USABLE IN COMBINATION WITH MEDICAL DIAGNOSIS APPARATUS

[75] Inventor: Hiroyuki Shibanuma, Tokyo, Japan

[73] Assignee: Kabushiki Kaisha Toshiba, Kawasaki, Japan

[21] Appl. No.: 340,373

[22] Filed: Nov. 14, 1994

[30] Foreign Application Priority Data

Nov. 29, 1993 [JP] Japan ................................. 5-298712

[51] Int. Cl.$^6$ .............................. H01N 7/18; A61B 1/04
[52] U.S. Cl. .......................... 348/65; 348/565; 600/109
[58] Field of Search ............................ 348/65, 71, 72, 348/73, 74, 75, 564, 565, 584; 600/104, 109, 113, 118, 160, 103

[56] References Cited

U.S. PATENT DOCUMENTS 5,196,928  3/1993  Karasawa et al. .................... 348/72
5,432,561  7/1995  Strubbe ............................ 348/565

Primary Examiner—Tommy P. Chin
Assistant Examiner—A. Au
Attorney, Agent, or Firm—Foley & Lardner

[57] ABSTRACT

An electronic endoscope apparatus which is used in combination with another medical diagnosis apparatus for medical diagnosis, includes a monitor for displaying the image based on a video signal from the endoscope or displaying both of the image based on a video signal from the endoscope and the image based on a video signal from the other medical diagnosis apparatus on the same screen, and a display switching controller for receiving the video signal from the other medical diagnosis apparatus and selectively switching the video signal to be displayed on the screen between the video signal from the endoscope and both of the video signals from the endoscope and the other medical diagnosis apparatus to display the image based on the selected video signal.

9 Claims, 9 Drawing Sheets

ELECTRONIC ENDOSCOPE APPARATUS USABLE IN COMBINATION WITH MEDICAL DIAGNOSIS APPARATUS

BACKGROUND OF THE INVENTION

1. Field of the Invention

This invention relates to an electronic endoscope apparatus, and particularly to the improvement of an image display technique when an electronic endoscope apparatus is used in combination with another medical diagnosis apparatus.

2. Description of Related Art

Recently, a medical diagnosis apparatus such as an X-ray medical diagnosis apparatus or the like has been progressively developed, and this progressive development of the medical diagnosis apparatus has increased the frequency of use of an electronic endoscope apparatus. The electronic endoscope apparatus includes a scope (endoscope) having an image pick-up element at the tip thereof, and when a biological object (patient) is examined, the scope is inserted into the body cavity of the object being examined to pick up an image in the body cavity for medical diagnosis.

At present, such an electronic endoscope apparatus has been more frequently used in combination with another medical diagnosis apparatus. For example, for medical diagnosis of colon by inserting a scope through a rectum, it frequently occurs that an operator cannot specify the position of the tip portion of the scope in the body cavity because the direction of the scope is unstable, that is, the operator cannot grasp the position in the body cavity under observation. Accordingly, in order to accurately specify the position of the tip portion of the scope, X-ray fluoroscopy has been tried for the object with an X-ray imaging apparatus. In this case, the operator checks the position of the scope of the endoscope apparatus in the body cavity while seeing an X-ray image obtained by the X-ray imaging apparatus.

Further, the endoscope apparatus is also used when a contrast medium is injected into a bile duct to obtain X-ray images of the bile duct. In this case, a catheter must be inserted into the bile duct to inject the contrast medium into the bile duct. At this time, an operator directs the tip portion of the scope to the bile duct portion while observing the image of the endoscope, inserts the catheter from a forceps port of the scope, and guides the catheter through the scope to the bile duct.

Where the endoscope apparatus is used in combination with the X-ray imaging apparatus for medical diagnosis, an object being examined is placed on a bed of the X-ray imaging apparatus, and an X-ray tube and an image intensifier are disposed in confronting relationship with each other so as to sandwich the object being examined therebetween. The image intensifier serves to convert X-rays transmitted through the object being examined to optical signals. The optical signals are imaged by a TV camera, and then displayed on the screen of an X-ray monitor. That is, a fluoroscopic image of the object being examined is displayed on the X-ray monitor.

Meanwhile, the endoscope apparatus is disposed near to the X-ray imaging apparatus, and the scope is inserted into the body cavity of the object being examined to display an image of the body cavity on an endoscope monitor. Through this operation, medical diagnosis using the X-ray imaging apparatus and the endoscope apparatus in combination is performed.

However, in the conventional diagnosis system as described above, the X-ray imaging apparatus and the endoscope apparatus are constructed and arranged independently of each other, and thus the operator must operate these apparatuses individually and independently. For example, the monitors of these apparatuses are disposed independently of and separately from each other, so that observing both monitors is laborious and cumbersome.

In order to overcome this disadvantage, the output of the TV camera may be connected to the monitor of the endoscope apparatus and the operator may selectively switch by hand the display on the monitor between the X-ray image and the endoscope image. This slightly reduced the labor imposed on the operator because the operator views only one monitor. However, the operator is still required to manually switch the display on the monitor, and the switching operation becomes more cumbersome when the switching operation between the X-ray image and the endoscope image is required more frequently. For example, during observation of the endoscope image, it is difficult to switch the display because the operator grips the scope in one hand. In this case, a foot switch may be used to avoid the above problem. However, operating the switch by foot entails risk of misoperation. Accordingly, this method is impractical.

In addition, since no endoscope image can be observed when the display is switched to the X-ray image, the risk of misoperation of the scope or misoperation of the treatment equipment increases.

As described above, when the conventional electronic endoscope apparatus as described above is used in combination with another medical diagnosis apparatus for medical diagnosis, the operator must view many monitors, and this imposes much labor on the operator. Further, even when the display can be selectively switched between the X-ray image and the endoscope image, it is difficult for the operator to manually switch the display.

SUMMARY OF THE INVENTION

An object of the present invention is to provide an electronic endoscope apparatus in which the display on a monitor is automatically adjusted so that an endoscope image and an image obtained by another medical diagnosis apparatus can be selectively displayed solely or in combination on the same screen.

In order to attain the above object, an electronic endoscope apparatus according to the present invention, in which an image of the body cavity of an object being examined is obtained by inserting a scope (endoscope) into the body cavity, includes display means for displaying the image based on an image signal output from the endoscope or displaying on the same screen the image based on image signals which are output from the endoscope and from another medical diagnosis apparatus, and display switching means for receiving the image signal from the other medical diagnosis apparatus to perform such a display switching operation that only the image based on the image signal from the endoscope (hereinafter referred to as "endoscope image") is displayed on the display means or both of the images based on the image signals which are output from the endoscope and the other medical diagnosis apparatus are displayed in combination on the display means in accordance with the received image signal.

According to the electronic endoscope apparatus thus constructed, when the endoscope apparatus is used in combination with another medical diagnosis apparatus such as an X-ray imaging (diagnosis) apparatus or the like, the image signal from the other medical diagnosis apparatus is taken into the endoscope apparatus, and it is judged on this image signal whether an image (X-ray image) actually exists in the image signal output from the other medical diagnosis apparatus (X-ray imaging apparatus). If an X-ray image is judged to exist, the endoscope image from the endoscope apparatus and the X-ray image from the X-ray imaging apparatus are displayed in parallel on the same monitor screen of the display means. If no image exists, the display on the display means is switched by the switching means so that only the endoscope image from the endoscope is displayed on the monitor screen. Accordingly, the operator is not required to manually switch the display on the display means, and thus an operation work can be improved.

DETAILED DESCRIPTION OF THE PREFERRED EMBODIMENTS

Preferred embodiment according to the present invention will be described hereunder with reference to the accompanying drawings.

In the first embodiment, for example when an endoscope apparatus and an X-ray imaging apparatus are used in combination to perform a medical diagnosis, a video (image) signal obtained by the X-ray imaging apparatus is taken into the endoscope apparatus, and the image based on the video signal from the X-ray imaging apparatus (hereinafter referred to as "X-ray image") and the image based on a video (image) signal from the endoscope apparatus (hereinafter referred to as "endoscope image") are displayed in parallel (in combination) on the same monitor only during an X-ray image actually existing in the image signal from the X-ray imaging apparatus. If no X-ray image exists in the video signal from the X-ray imaging apparatus, only the endoscope image is displayed on the monitor.

Figure 2:
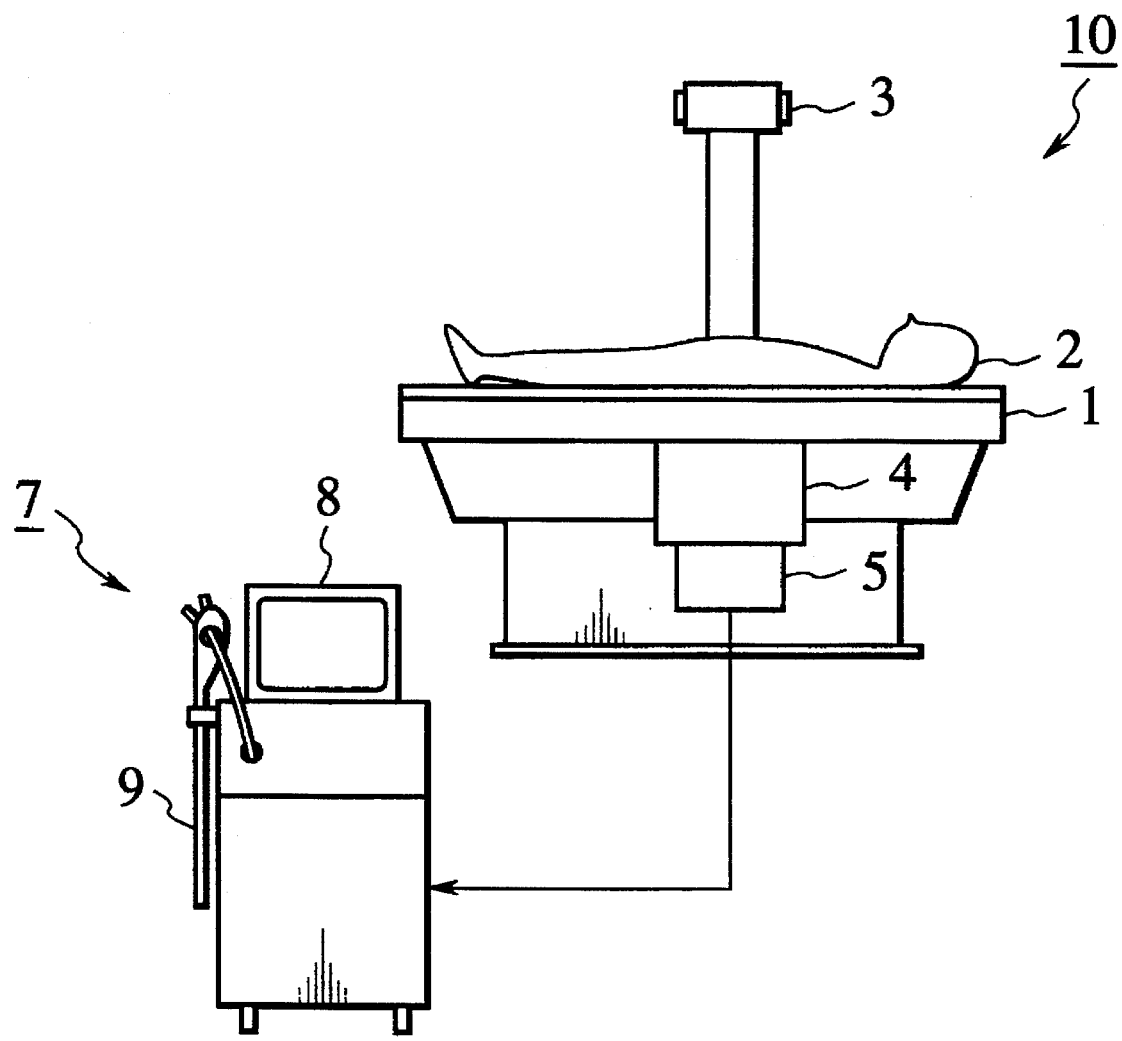
FIG. 2 is a schematic diagram showing a connection arrangement of an X-ray imaging apparatus and an endoscope apparatus in the first embodiment according to the present invention.

FIG. 2 is a schematic diagram showing a connection arrangement of the X-ray imaging apparatus and the endoscope apparatus.

As shown in FIG. 2, an object being examined (hereinafter referred to as "object") 2 is placed on a bed 1 of an X-ray imaging apparatus 10, and an X-ray tube 3 and an image intensifier 4 are arranged so as to face each other and sandwich the object 2 therebetween. The image intensifier 4 serves to convert X-rays transmitted through the object 2 to optical signals. The optical signals are imaged by a TV camera 5, and then supplied as a video (image) signal to a monitor 8 of the endoscope apparatus 7. The endoscope apparatus 7 has a scope (endoscope) 9, and the endoscope 9 is inserted into the body cavity of the object 2 to display the image of the body cavity on the monitor 8. Through this operation, the medical diagnosis using the endoscope apparatus 7 and the X-ray imaging apparatus 10 in combination is performed.

Figure 1:
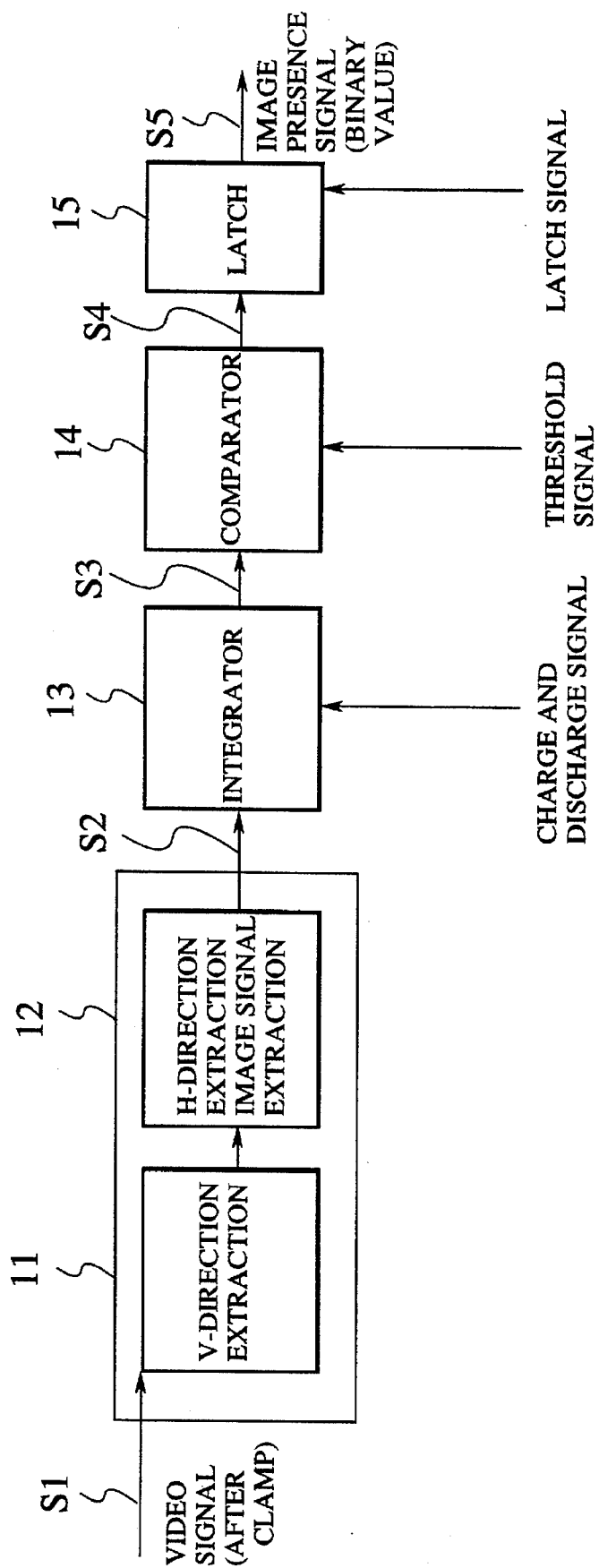
FIG. 1 is block diagram showing an image presence judgment circuit for generating an image-presence signal in a first embodiment according to the present invention.

FIG. 1 is a block diagram showing a circuit (switching means) for judging whether an X-ray image exists in the video signal from the X-ray imaging apparatus 10. As shown in FIG. 1, the circuit (switching means) includes a V-direction extract unit 11 for extracting vertical direction components from the video signal of the X-ray imaging apparatus, an H-direction extract unit 12 for extracting horizontal direction components from the video signal of the X-ray imaging apparatus, an integrator 13 for integrating the signal of each of the V and H direction components every field, a comparator 14 for comparing the integration result of the integrator 13 with a threshold (reference) value to judge whether the integration result is larger than the threshold value, and a latch 15 for determining the presence or absence of an X-ray image in the video signal from the X-ray imaging apparatus on the basis of the comparison result and outputting a signal representing the presence or absence of the X-ray image (hereinafter referred to as "X-ray image presence signal").

Next, the operation of this embodiment will be described with reference to a timing chart of FIG. 3.

Figure 4A:
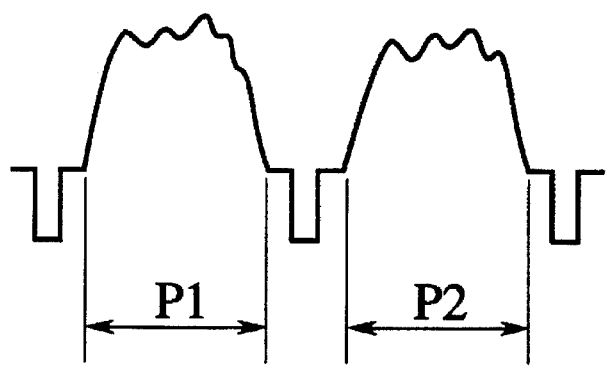
FIGS. 4A and 4B are diagrams showing a video (image) signal extract and clamp processing in the first embodiment.
Figure 4B:
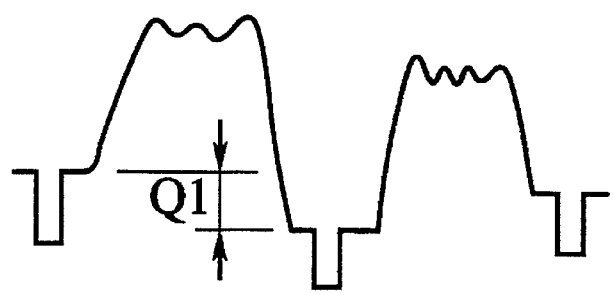

Upon input of the video signal from the X-ray imaging apparatus to the endoscope apparatus, a clamp processing (DC reproduction) is first performed to meet the blanking level between image signals of the video signal, and then the processed signals are supplied to the V-direction extract unit 11 and the H-direction extract unit 12. The clamp processing is used to meet the DC amplitude among the image signals of the video signal. For example, when the DC amplitude of each image signal is varied by Q1 at a 1 H period as shown in FIG. 4B, the clamp processing is carried out to suppress this variation and make all the image signals have a fixed DC amplitude.

Figure 3:
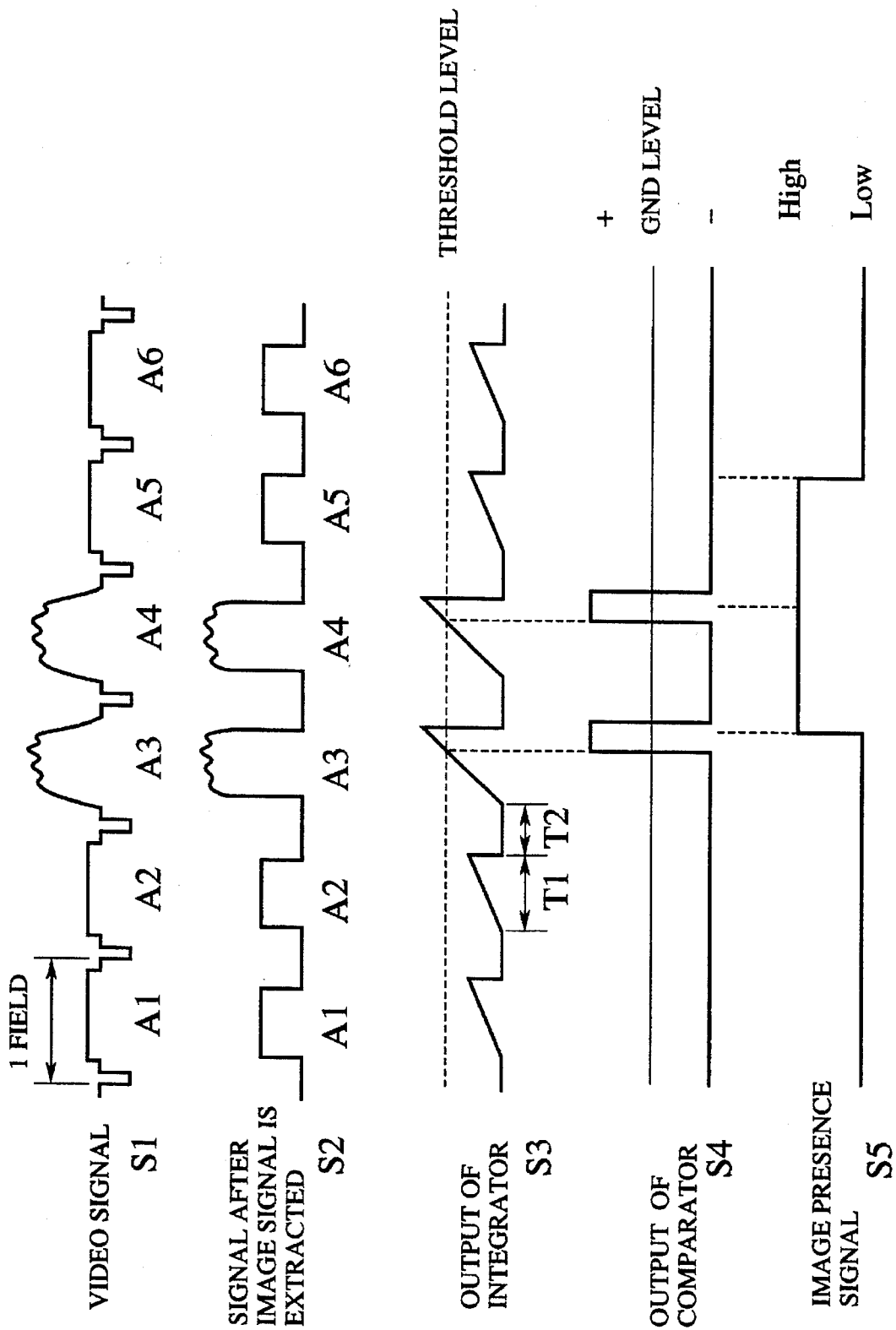
FIG. 3 is a timing chart showing an operation of the first embodiment.

When supplied with a video signal S1 shown in FIG. 3, each of the V-direction extract unit 11 and the H-direction extract unit 12 extracts only the image signals of each field. Each image signal contains an image component and other blanking signals, and the image component exists only in an area P1 (P2) as shown in FIG. 4A while the blanking signals exist in the other areas. Therefore, in the V-direction and H-direction extract units 11 and 12, the blanking portion is removed to output a signal S2 having only the image components.

In FIG. 3, any one of the image signals in the horizontal and vertical directions is illustrated on the stage of the video signal S1. Both image signals in the horizontal and vertical directions exist actually, however, the same subsequent processing is performed for these image signals. Therefore, the other image signal is omitted from FIG. 3.

Thereafter, integration of signal values of each field is performed in the integrator 13 to obtain a signal S3 representing the integration result. Here, the video signal S1 contains some fields having X-ray images and other fields having no X-ray images. In the case shown in FIG. 3, an X-ray image exists in areas (fields) A3 and A4, however, no X-ray image exists in areas (fields) A1, A2, A5 and A6.

Accordingly, the output signal S3 (representing the integration value) of the integrator becomes larger for the areas A3 and A4, and it exceeds a threshold level. On the other hand, the signal S3 for the other areas becomes smaller than the threshold level. In FIG. 3, T1 represents an integration time, and T2 represents a discharge time.

In the comparator 14, the integration value (signal S3) is compared with the threshold level to output a signal S4 representing the comparison result. The signal S4 is kept positive (plus) in polarity for a period when the integration value exceeds the threshold level while it is kept negative (minus) in polarity for the other period. The signal S4 thus obtained is output to the latch 15.

The latch 15 is supplied with the signal S4 to generate and output a signal S5 holding the output of the comparator 14 (signal S4). That is, when the signal S4 becomes positive, the signal S5 of the next field becomes "High". In this case, the output signal S4 of the comparator becomes positive in the fields A3 and A4, so that the output signal S5 of the latch 15 becomes "High" in the fields A4 and A5. If the signal S5 is output as an image presence signal to an image display system of the endoscope apparatus, this signal is usable as a display switching signal for the X-ray imaging apparatus.

Figure 5A:
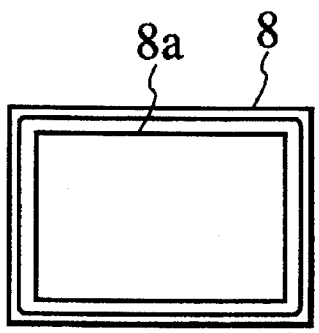
FIGS. 5A and 5B are schematic views of displays on a screen in the first embodiment.
Figure 5B:
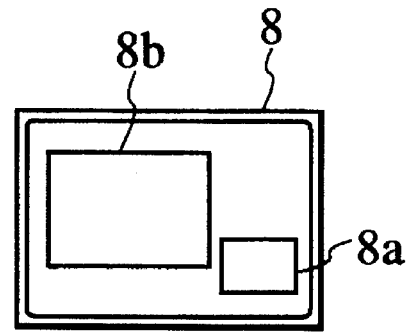

In this case, if the image presence signal is "High", presence of an X-ray image is judged. On the other hand, if the image presence signal is "Low", absence of the X-ray image is judged. Accordingly, the following display switching operation may be used in accordance with the logic state of the signal S5. That is, when the signal S5 is "Low", an endoscope image 8a may be fully displayed over the frame of the screen as shown in FIG. 5A. On the other hand, when the signal S5 is "High", an X-ray image 8b is displayed on a main frame of the screen while the endoscope image 8a is displayed on a sub frame of the screen (i.e., a main-sub frame display (TV-in-TV) mode is used). With this operation, the operator is not required to manually carry out the display switching operation because the display switching operation is automatically performed. The TV-in-TV mode enables the operator to observe the endoscope image at all times, thereby avoiding a risk such as a misoperation of the endoscope or the treatment equipment inserted in the body cavity.

As described above, according to this embodiment, the period when an X-ray image exists actually is detected on the basis of the video signal obtained by the X-ray imaging apparatus, and the display switching operation is carried out so that the X-ray image is displayed in combination with the endoscope image only for that period. Accordingly, the image display can be automatically switched, and the labor imposed on the operator can be reduced.

In the embodiment as described above, the presence or absence of the X-ray image is judged on the basis of the video signal output from the X-ray imaging apparatus. However, the presence or absence of the X-ray image may be judged using a signal representing irradiation of X-rays from the X-ray imaging apparatus. That is, the irradiation of the X-rays means that an imaging operation is carried out, and it follows the output of an X-ray image. However, the X-ray imaging apparatus and the endoscope apparatus which are generally used are not equipped with a terminal for outputting a signal representing the X-ray irradiation and a terminal for receiving the signal, respectively.

On the other hand, according to the embodiment, the video signal output from the X-ray imaging apparatus itself is used as a signal for judging the presence or absence of the X-ray image, and thus the connection arrangement between the endoscope apparatus and the X-ray imaging apparatus can be facilitated. That is, the general X-ray imaging apparatus and endoscope apparatus have a video-signal output terminal and a video-signal input terminal, and thus these apparatuses can be connected to each other using no special connection terminal.

Figure 6:
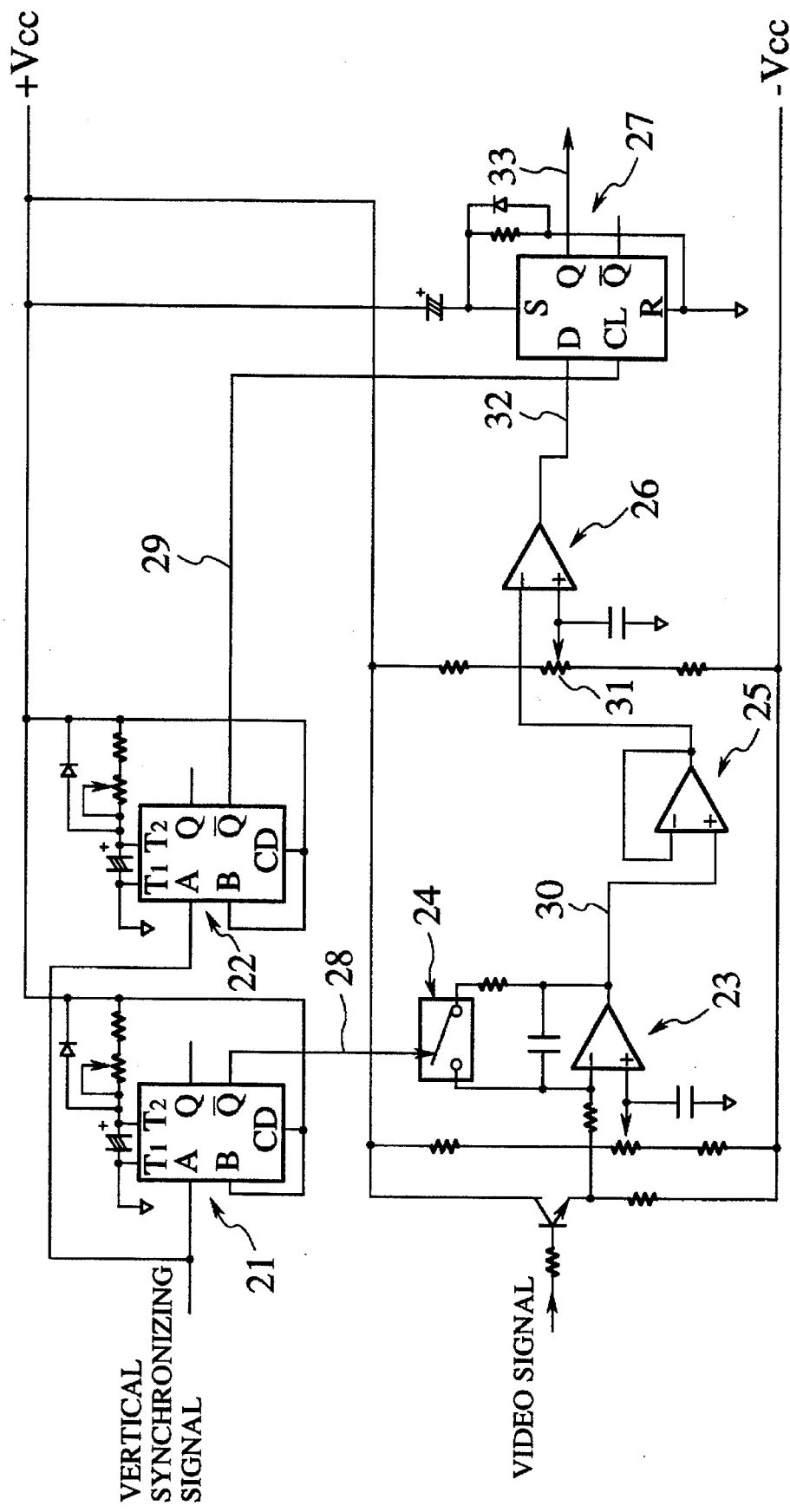
FIG. 6 is a detailed circuit diagram of the circuit shown in FIG. 1.

FIG. 6 is a detailed circuit diagram of the circuit shown in FIG. 1. In FIG. 6, reference numeral 21 represents an element for generating a charge and discharge signal from the vertical synchronizing signal and outputting it to a subsequent stage. Reference numeral 28 represents the charge and discharge signal. Reference numeral 24 represents a switch whose switch on/off operation is performed on the basis of the charge and discharge signal 28, and the charging and discharging operations of an integrator 23 are switched to each other by the switch 24. The output of the integrator 23 is passed through a buffer 25 and then output to a comparator 26 to be compared with a threshold level which is determined by a variable resistance 31. The output 32 of the comparator 26 is supplied to a latch 27. The latch 27 is also supplied with a latch signal 29 which is output from the element 22. An image presence signal 33 is output from the latch 27. The operation of the actual circuit is performed according to the signal flow as described above.

In FIG. 6, the switching operation of the switch 24 is controlled on the basis of the charge and discharge signal 28 to perform the switching operation between the charging and discharging of the integrator 23, thereby extracting the image components of the V direction. The extraction of the image components in the H direction is omitted from FIG. 6. The extraction in the H direction is not necessarily required, and it is sufficient to extract at least the extraction in the V direction.

Figure 7:
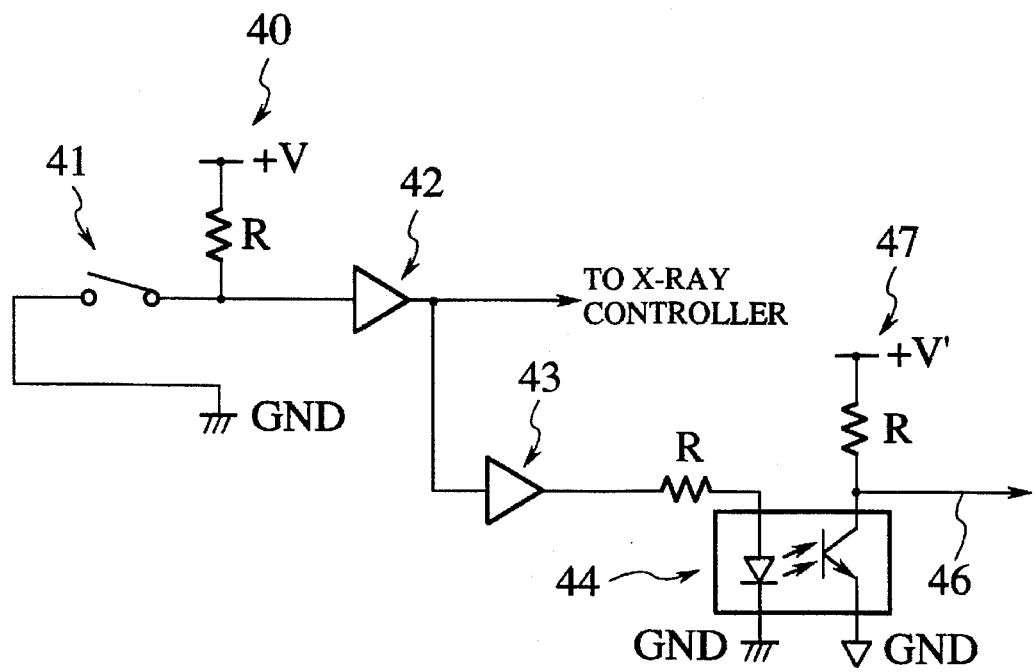
FIG. 7 is a circuit diagram for a first modification of the first embodiment.

FIG. 7 shows a first modification of the first embodiment as described above. In this modification, an X-ray on/off signal of a fluoroscopy switch or foot switch which is provided on a console of the bed 1 of the X-ray imaging apparatus 10 is supplied to the endoscope apparatus through an X-ray on/off signal detection circuit to switch the display on the monitor 8.

In the circuit diagram shown in FIG. 7, the on/off signal from the fluoroscopy switch 41 is transmitted through a buffer 42 to an X-ray controller. On the other hand, a signal from the buffer 42 is supplied through a buffer 43 to a photocoupler (insulating means) 44, and further supplied through the photocoupler to a circuit at an endoscope system side. The supplied signal is used as an X-ray on/off signal 46 to perform an image display switching operation of the monitor 8. Reference numeral 40 represents a power source for an X-ray control system, and reference numeral 47 represents a power source for the endoscope system.

Figure 8:
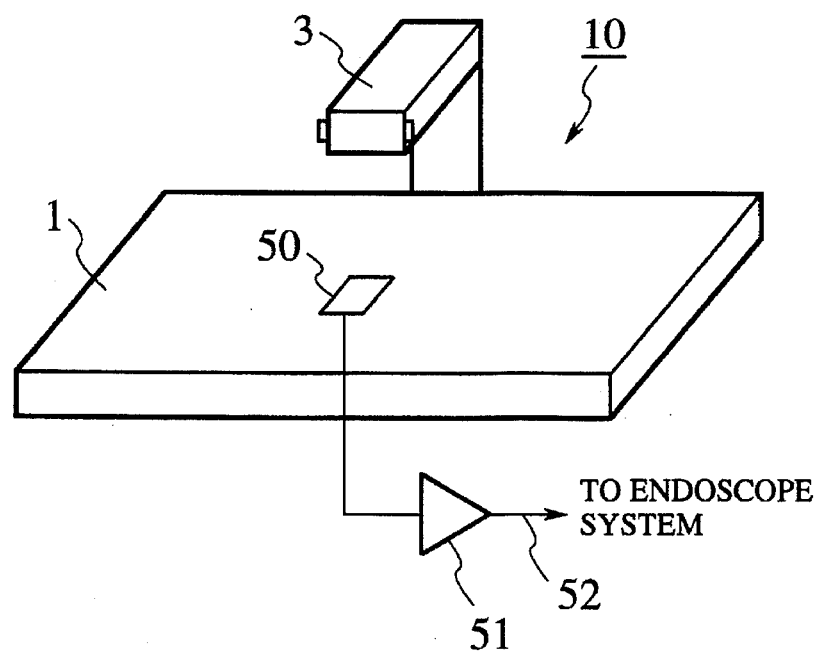
FIG. 8 is a circuit diagram for a second modification of the first embodiment.

FIG. 8 shows a second modification of the first embodiment. In this modification, an X-ray detector 50 (for example, a CCD having sensitivity to X-ray wavelength band or the like) is disposed on the bed 1 of the X-ray imaging apparatus, and the output signal of the X-ray detector 50 is transmitted as an X-ray on/off signal through an amplifier 51 to the endoscope system 7. The display switching operation of the monitor 8 is performed on the basis of the X-ray on/off signal 52.

Figure 9:
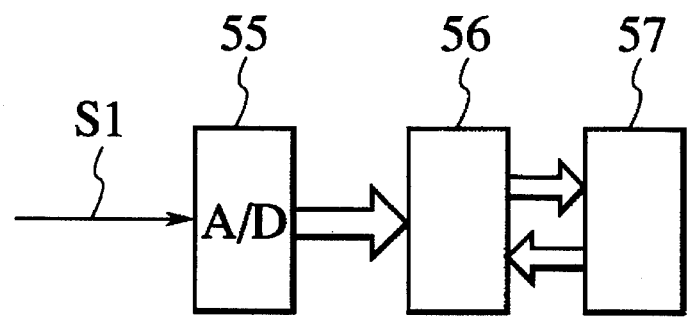
FIG. 9 is a circuit diagram for a third modification of the first embodiment.

FIG. 9 shows a third modification of the first embodiment. In this modification, the video signal S1 from the X-ray imaging apparatus is converted to digital values (digitally converted) by an A/D converter 55, and stored in a field memory 56. Thereafter, the image data stored in the field memory 56 are calculated by a processor 57, and the display image switching operation of the monitor is performed on the basis of the calculation result. In the calculation, for example, a central portion of the image is picked up, all data in the area are summed up, and the sum value thus obtained is compared with a predetermined numerical value to judge the presence or absence of the X-ray image.

As a further modification of the above modification, it may be considered that the digitalized image signal is directly calculated with no memory (the digital values are summed up using a hardware structure).

Figure 10:
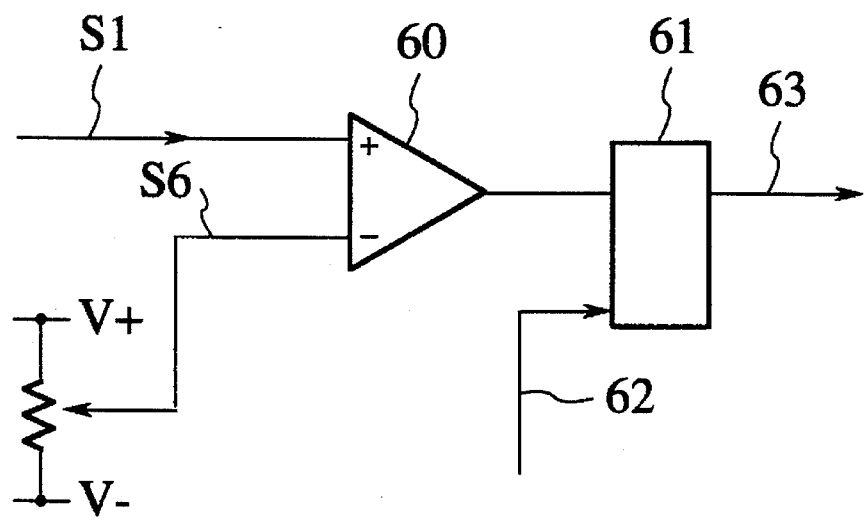
FIG. 10 is a circuit diagram for a fourth modification of the first embodiment.

FIG. 10 is a fourth modification of the first embodiment.

In this modification, the video signal S1 from the X-ray imaging apparatus is directly compared with a predetermined value without being integrated, and the image display switching operation is performed on the basis of the comparison result.

In FIG. 10, the X-ray video signal S1 is compared with a comparison signal S6 in a comparator 60, and the output of the comparator 60 is supplied to a latch 61. A latch signal 62 is supplied to the latch 61, and an X-ray on/off signal is output from the latch 61.

In this modification, the comparison is carried out at the 1H period (about 63.5 μsec (NTSC system)), so that a response speed is high and the circuit construction is simplified.

Figure 11:
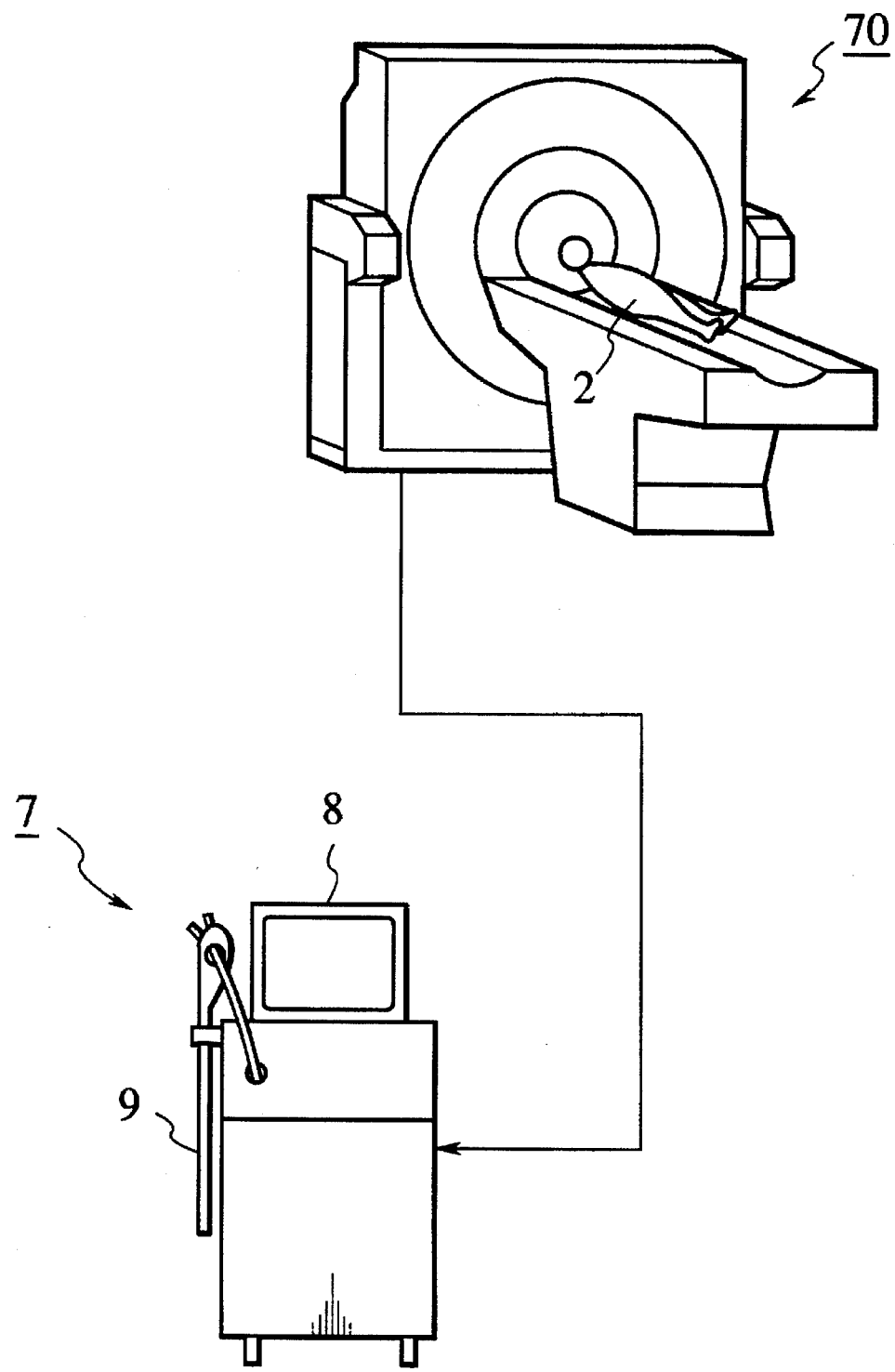
FIG. 11 is a schematic diagram showing a connection arrangement of an MRI apparatus and the endoscope apparatus in a second embodiment according to the present invention.

FIG. 11 shows a second embodiment according to the present invention. In this embodiment, an MRI apparatus is used as another medical diagnosis apparatus in combination with the endoscope apparatus.

The same construction as the first embodiment and the first to fourth modifications as described above is applicable to the second embodiment, and the duplicate description thereof is omitted.

Figure 12:
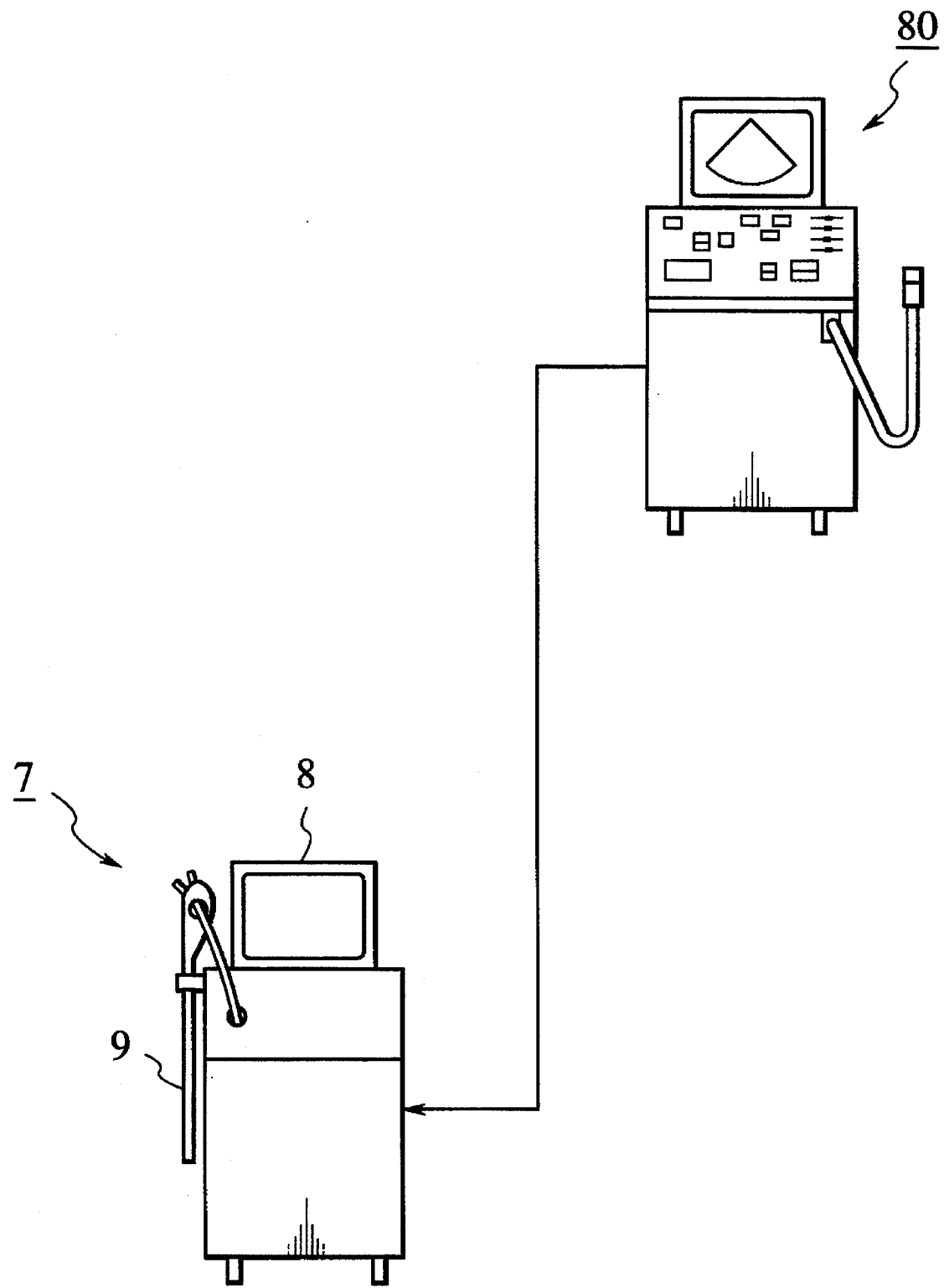
FIG. 12 is a schematic diagram showing a connection arrangement of an ultrasonic diagnosis apparatus and the endoscope apparatus in a third embodiment according to the present invention.

FIG. 12 shows a third embodiment of the present invention. In this embodiment, an ultrasonic diagnosis apparatus 80 is used as another medical diagnosis apparatus in combination with the endoscope apparatus.

The same construction as the first embodiment and the first to fourth modifications as described above is applicable to the third embodiment, and the duplicate description is omitted.

In the embodiments as described above, only one medical diagnosis apparatus is used in combination with the endoscope apparatus. However, this invention is not limited to the above embodiments (only one medical diagnosis apparatuses is used in combination with the endoscope apparatus), and plural other medical diagnosis apparatuses may be used in combination with the endoscope apparatus.

According to this invention as described above, in a case where an endoscope apparatus is used in combination with another medical diagnosis apparatus for diagnosis, the image display on a monitor is switched so that both of an endoscope image and an image supplied from the other medical diagnosis apparatus are displayed In parallel on the monitor only when the image is actually transmitted from the other medical diagnosis apparatus, and only the endoscope image is displayed on the monitor in the other cases. Accordingly, the operator is not required to manually switch the display content on the monitor, so that the operation performance can be improved and no misoperation is induced.

What is claimed is:

1. An electronic endoscope apparatus for inserting an endoscope into a body cavity of an object being examined to obtain an image of the body cavity and to display the obtained image, comprising:

display means for displaying on a screen an image based on a video signal from said endoscope or concurrently displaying on the screen images based on video signals from said endoscope and another medical diagnosis apparatus; and display switching means for receiving a video signal from said other medical diagnosis apparatus and selectively switching a video signal to be displayed on said display means between the video signal from said endoscope and the video signals from said endoscope and said other medical diagnosis apparatus to display an image based on a selected one of the video signal from said endoscope and the video signals from said endoscope and said other medical diagnosis apparatus, said display switching means including, integration means for extracting image components in a vertical direction from the video signal from said other medical diagnosis apparatus and integrating the image components for each field, and comparison and judgment means for comparing the integration result of said integration means with a predetermined reference value to judge whether the integration result is larger than the predetermined reference value, both of the images based on the video signals from said endoscope and said other medical diagnosis apparatus being displayed concurrently on the screen when the integration result is judged to be larger than the predetermined reference value.

2. The electronic endoscope apparatus as claimed in claim 1, wherein said display means has a multi-frame display function in which the images based on the video signals from said endoscope apparatus and said other medical diagnosis apparatus are displayed on multi-frames in a TV-in-TV mode.

3. The electronic endoscope apparatus as claimed in claim 1, wherein said other medical diagnosis apparatus comprises at least one of an X-ray diagnosis apparatus, an ultrasonic diagnosis apparatus and an MRI apparatus.

4. The electronic endoscope apparatus as claimed in claim 3, wherein said display means has a multi-frame display function in which the images based on the video signals from said endoscope apparatus and said other medical diagnosis apparatus are displayed on multi-frames in a TV-in-TV mode.

5. The electronic endoscope apparatus as claimed in claim 1, wherein said integration means extracts image components in vertical and horizontal directions from the video signal output from said other medical diagnosis apparatus and integrates the image components every field.

6. The electronic endoscope apparatus as claimed in claim 5, wherein said other medical diagnosis apparatus comprises at least one of an X-ray diagnosis apparatus, an ultrasonic diagnosis apparatus and an MRI apparatus.

7. The electronic endoscope apparatus as claimed in claim 6, wherein said display means has a multi-frame display function in which the images based on the video signals from said endoscope apparatus and said other medical diagnosis apparatus are displayed on multi-frames in a TV-in-TV mode.

8. The electronic endoscope apparatus as claimed in claim 5, wherein said display means has a multi-frame display function in which the images based on the video signals from said endoscope apparatus and said other medical diagnosis apparatus are displayed on multi-frames in a TV-in-TV mode.

9. An electronic endoscope apparatus for inserting an endoscope into a body cavity of an object being examined to obtain an image of the body cavity and to display the obtained image, comprising:

- a display unit for displaying on a screen an image based on a video signal from said endoscope or concurrently displaying on the screen images based on video signals from said endoscope and another medical diagnosis apparatus; and
- display switching circuitry for receiving a video signal from said other medical diagnosis apparatus and selectively switching a display video signal to be displayed on said display unit between the video signal from said endoscope and the video signals from said endoscope and said other medical diagnosis apparatus to display an image based on the display video signal selected by said display switching circuitry, said display switching circuitry including,
- an integrator for extracting image components in a vertical direction from the video signal from said other medical diagnosis apparatus and integrating the image components for each field to produce an output signal, and
- a comparison and judgment circuit for comparing the output signal with a predetermined reference value to judge whether the output signal is larger than the predetermined reference value, and, when the output signal is judged to be larger than the predetermined reference value, both images based on the video signals from said endoscope and said other medical diagnosis apparatus being displayed concurrently on the screen.

* * * * *